United States Patent
Darling

(10) Patent No.: US 11,901,084 B2
(45) Date of Patent: *Feb. 13, 2024

(54) SYSTEM AND METHOD OF EVENT SEQUENCING AND RECORD AUTOMATION FOR HEALTHCARE

(71) Applicant: Matthew Ross Darling, O'connor (AU)

(72) Inventor: Matthew Ross Darling, O'connor (AU)

(73) Assignee: HUMANETIX IP PTY LTD, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/946,251

(22) Filed: Sep. 16, 2022

(65) Prior Publication Data
US 2023/0187082 A1  Jun. 15, 2023

Related U.S. Application Data

(63) Continuation of application No. 16/889,593, filed on Jun. 1, 2020, now abandoned, which is a continuation
(Continued)

(51) Int. Cl.
*G16H 70/20* (2018.01)
*G16H 20/13* (2018.01)
(Continued)

(52) U.S. Cl.
CPC ............. *G16H 70/20* (2018.01); *G16H 20/13* (2018.01); *G16H 50/70* (2018.01); *G16H 70/60* (2018.01);
(Continued)

(58) Field of Classification Search
CPC ........ G16H 70/20; G16H 20/13; G16H 50/70; G16H 70/60; G16H 10/60; G16H 40/20; G16H 50/20; G16Z 99/00
See application file for complete search history.

(56) References Cited

U.S. PATENT DOCUMENTS

2005/0240441 A1* 10/2005 Suzuki ................... G16H 40/20
705/2

FOREIGN PATENT DOCUMENTS

WO   WO-2005036447 A2 *  4/2005  ............ A61M 5/142

OTHER PUBLICATIONS

Emory A. Fry, MD and Leslie A. Lenert, MD. MASCAL: RFID Tracking of Patients, Staff and Equipment to Enhance Hospital Response to Mass Casualty Events. AMIA Annu Symp Proc. 2005; 2005: 261-265 (Year: 2005).*

* cited by examiner

*Primary Examiner* — Linh Giang Le
(74) *Attorney, Agent, or Firm* — Ladas & Parry LLP

(57) ABSTRACT

Methods and devices are provided for healthcare action sequencing and record keeping. The method may involve scanning a patient care area for tags for entities present in the area, a given patient being located in the area. The method may involve reading identity data from a tag, in response to detecting the tag for an entity in the area. The method may involve receiving input data regarding the given patient by a healthcare personnel via a user-interface. The method may involve communicating with a management system that includes a first database storing rules for how patients with known sets of conditions are to be cared for, a second database storing rules for how the input data are to be used, and a third database storing rules relating to procedures and restrictions for the healthcare personnel.

19 Claims, 9 Drawing Sheets

Related U.S. Application Data of application No. 15/427,605, filed on Feb. 8, 2017, now Pat. No. 10,671,702, which is a continuation of application No. 13/579,097, filed as application No. PCT/US2011/024933 on Feb. 15, 2011, now abandoned.

(60) Provisional application No. 61/304,758, filed on Feb. 15, 2010.

(51) Int. Cl.
  *G16H 50/70* (2018.01)
  *G16H 70/60* (2018.01)
  *G16Z 99/00* (2019.01)
  *G16H 40/20* (2018.01)
  *G16H 50/20* (2018.01)
  *G16H 10/60* (2018.01)

(52) U.S. Cl.
  CPC .............. *G16Z 99/00* (2019.02); *G16H 10/60* (2018.01); *G16H 40/20* (2018.01); *G16H 50/20* (2018.01)

Task Details

Patient Name: Tom Wood

Bed ID: L

Medication Required

Available for collection at dispensary

Time remaining: ~ 4 minutes

Status: Assigned to Janey X. Smith

Please proceed to the dispensary to collect medication

FIG. 4

SYSTEM AND METHOD OF EVENT SEQUENCING AND RECORD AUTOMATION FOR HEALTHCARE

BACKGROUND

Computerized systems to support specific procedures, such as emergency triage, radiology and pathology, are known in the art of the healthcare industry. Patient care databases are also common place. While there are a large number of technologies and computerized systems in use in and available to the healthcare industry, existing technologies do not in practice effectively streamline and support patient care by nurses.

The computer systems in place often constitute a bewildering array of disparate systems built for and by specialist stakeholders. Nurses are frequently overburdened with records and charts which are repetitive, time-consuming and difficult to interpret, leading to errors which may be harmful or even fatal to patients, unnecessary stress, loss of job satisfaction, and high rates of worker turnover.

There are small systems in the art designed to help reduce errors in the administration of medications which use barcode reading to provide systematized assurance that the correct medication is administered to the intended patient. This system is dependant upon the availability of bar code scanners at every bed or with every nurse and with every patient.

Computerized bedside monitoring systems are often used in Intensive Care Units (ICUs) at hospitals. These systems record biological signs and frequently record medications given by drip, as well as automated nutrition. Another feature of monitoring systems may include alarms to alert nursing staff to possible deterioration in patient condition and to alert other hospital staff, such as doctors not at the bedside, to ensure rapid response. However these systems are relatively unintelligent in that they do not support the nursing and medical staff by prioritizing them.

Hospital administrators have made attempts to monitor patient care activities with a variety of surveillance technologies. These systems have proved extremely unpopular with nurses, as they are also unintelligent, simply monitoring and recording, rather than helping. Accordingly, there remains a need for technologies and methodologies for addressing the above-described issues.

SUMMARY

In accordance with one or more embodiments and corresponding disclosure thereof, various aspects are described in connection with a method for healthcare action sequencing by a bedside device or similar apparatus. For example, the method may involve scanning a patient care area (e.g., a patient room of a hospital ward) for tags for entities (e.g., a healthcare personnel, a patient, a medication container, a physical file for the patient, etc.) present in the area, a given patient being located in the area. The method may involve reading identity data from a tag (e.g., a radio-frequency identification (RFID) tag, a bar-coding, a magnetic stripe, a bluetooth tag, etc.), in response to detecting the tag for an entity in the area. The method may involve receiving input data regarding the given patient by at least one healthcare personnel (e.g., a nurse, a doctor, etc.) via a user-interface.

The method may involve sending the identity data and the input data to a management system that includes a first database storing first rules for how patients with known sets of conditions are to be cared for, a second database storing second rules for how the input data are to be used, and a third database storing third rules relating to procedures and restrictions for the at least one healthcare personnel. The method may involve receiving action data for the given patient from the management system based at least in part on (a) the identity data, (b) the input data, and (c) at least one of the first rules, the second rules, and the third rules. The method may involve displaying information (e.g., task details for at least one task to be performed by the at least one healthcare personnel, or a patient care procedure and confirmation screen) on the user-interface based at least in on the received action data. In related aspects, there is provided a bedside device for healthcare action sequencing comprising at least one processor configured to perform the above-described process.

In accordance with one or more aspects of the embodiments described herein, there is a method for healthcare action sequencing by a management system or apparatus. For example, the method may involve receiving identity data regarding a given patient from a bedside computer in a patient care area, the bedside computer reading the identity data from a tag for an entity in the area. The method may involve receiving input data regarding the given patient by at least one healthcare personnel. The method may involve cross-referencing the identity data and the input data with a first database storing first rules for how patients with known sets of conditions are to be cared for, a second database storing second rules for how the input data are to be used, and a third database storing third rules relating to procedures and restrictions for the at least one healthcare personnel. The method may involve determining action data for the given patient based at least in part on the cross-referencing of the identity data and the input data with the first database, the second database, and the third database. The method may involve sending the action data for the given patient to the bedside computer. In related aspects, there is provided a management system for healthcare action sequencing comprising at least one processor configured to perform the above-described process.

To the accomplishment of the foregoing and related ends, one or more aspects comprise the features hereinafter fully described and particularly pointed out in the claims. The following description and the annexed drawings set forth in detail certain illustrative aspects and are indicative of but a few of the various ways in which the principles of the aspects may be employed. Other novel features will become apparent from the following detailed description when considered in conjunction with the drawings and the disclosed aspects are intended to include all such aspects and their equivalents.

BRIEF DESCRIPTION OF THE DRAWING

FIG. 4 illustrates an exemplary patient information screen.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Figure 1:
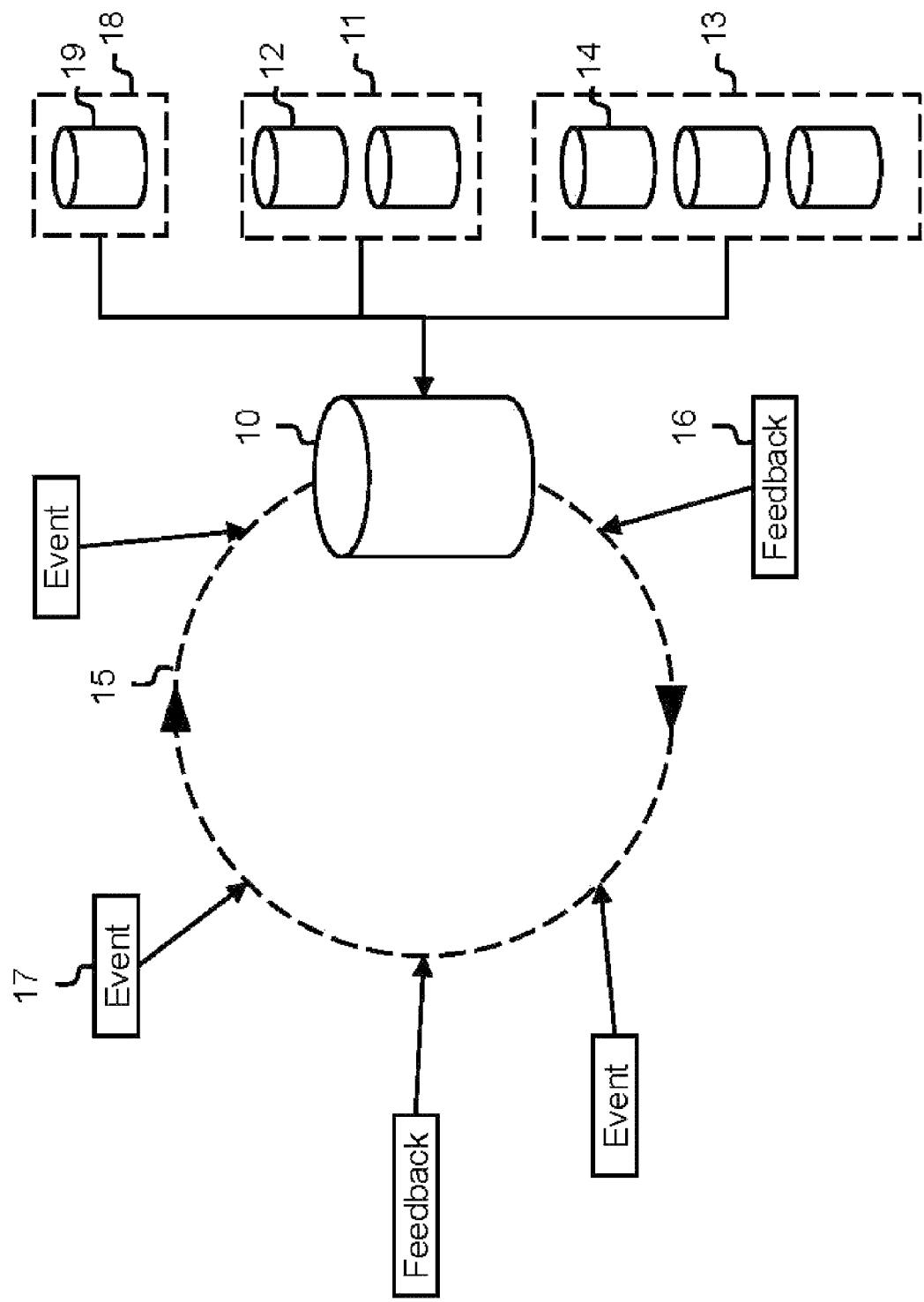
FIG. 1 provides a system overview.

FIG. 1 describes a management system that takes as input feedback 16 from nursing staff, doctors and specialists as well as device events 17 such as RFID trigger and data inputs, blood pressure and oxygen level monitors and their data regarding a specific patient.

This management system may monitor a subset of or all patients in a hospital including their care in specialist services such as therapeutic or diagnostic services. The main computer control application 10 initiates a feedback cycle 15 in which input from devices called events 17 and feedback from care personnel 16 are collected and returned to the application 10 for processing.

The management application 10 then uses the input 16, 17 in conjunction with databases of rules 18, 11, 13 that help the management system determine the most effective way to care for patients in the hospital.

There are three main sets of rules databases. The first set 18 contains databases that contain rules and procedures for how a patient with a known set of conditions is to be cared for. The second set of database 11 contain rules that govern how device events 17 and care personnel feedback 16 are reacted to, prioritized and managed. The third set of databases 13 contains rules relating to the limitations and operating procedures for care personal depending on their specific role.

An example of these databases working interactively with the control application 10 may be illustrated with a medication treatment scenario. A database containing standard procedure for the administration and dosage of a particular medication may be included in the main care databases 18. The procedure may dictate that a particular drug, at a particular dosage be administered to a particular patient at a particular time interval.

The patient care management system 10 may dictate that the nurse for that patient administer the drug within an optimal window of time. The management system 10 anticipates the arrival of the nurse at a particular patient's bed at a particular time, and identifies both the nurse and the patient by the use of RFID tags that they are wearing. An RFID tag attached to the medication may also be used to verify the administration of required medication. The event rules databases 11 may be consulted to ensure that the medication has been administered within appropriate guidelines and reminders, and if needed, alarms are generated to ensure the mediation is delivered on time. Also, a drug usage database of rules 12 within the set of events databases 11 may be consulted to ensure that a particular drug may need to be administered more than an hour before meal times to avoid nausea or interactions with food affecting absorption.

The set of databases regarding procedures for particular roles 13 may also be consulted to support the nurse in supplying a clinically appropriate action in a timely fashion as the patient's condition changes and ensuring escalation to a doctor when needed.

Figure 2:
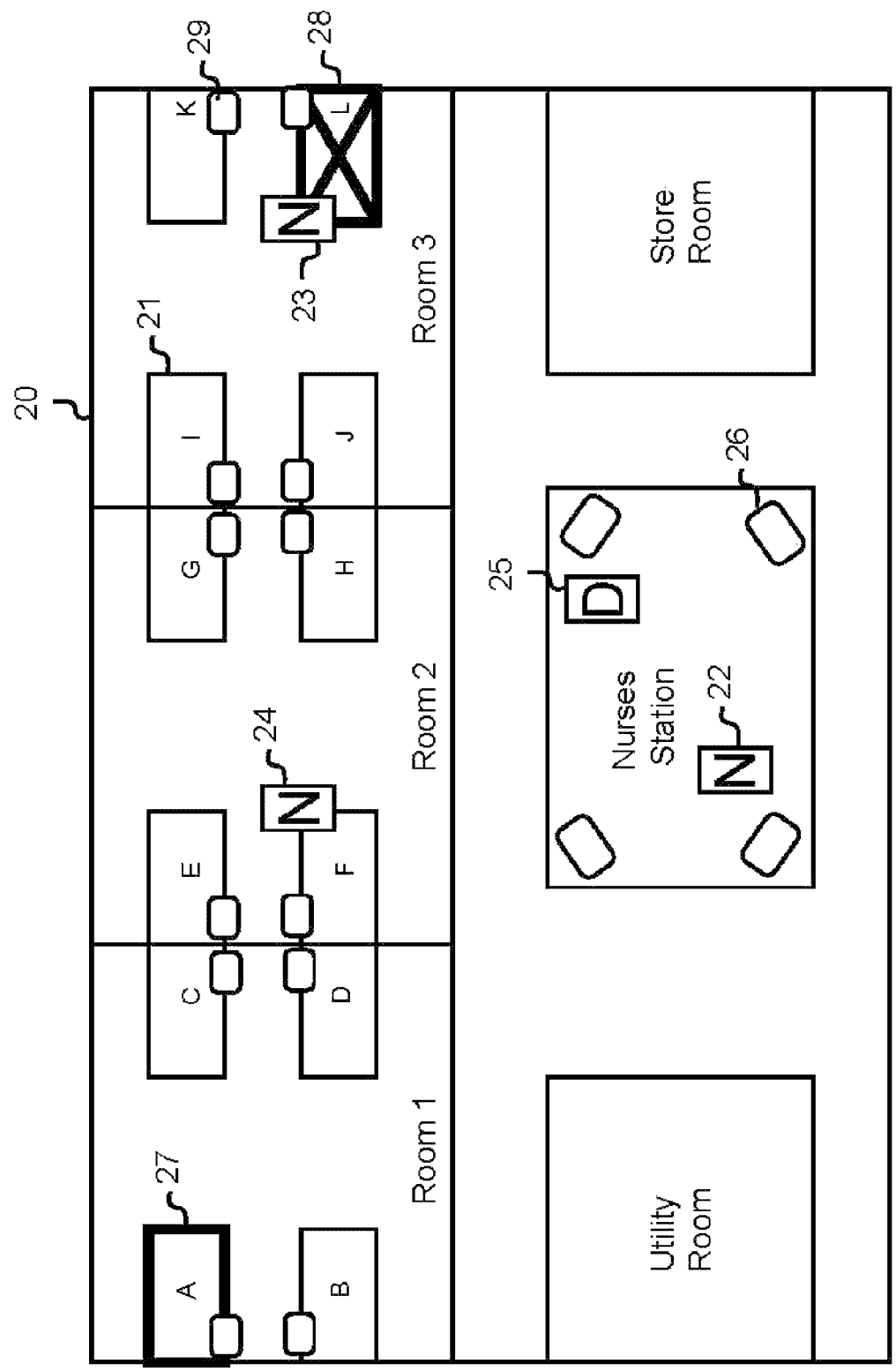
FIG. 2 illustrates an exemplary ward feedback overview screen.

FIG. 2 is an example representation of an output from the control application 10 that may be displayed on monitors throughout a hospital ward. The screen comprises a basic representation of the floor plan of a ward 20 identical to the ward being serviced by the management software 10. In this example there are three patient rooms, corridors, a nurses' station and a store room and a utility room. Each ward patient room comprises four beds 21. Each bed has a bedside computer system 29. Additional computers 26 that can also access the management system 10 are located at the nurses' station and dispensary.

The example representation also contains icons that represent the approximate location of nurses 23, 22, 24 and doctors 25 on the ward. This information is gathered and monitored by the use of RFID tags that the nurses and doctors wear and RFID readers attached to each workstation 26 or bedside computer 29.

In this example scenario there in one nurse in room three 23, one nurse in room two 24 and another nurse in the nursing station 22. There is also a doctor 25 at the nursing station. In this example scenario the management application 10 has collected device events 17 and nurse feedback 16 that relate to the patient in bed L 28 in room three of the ward and determined that the patient requires critical action. The outline of the bed is made with bold lines on the screen and a flashing cross draws a viewer's eyes to that bed so that all available staff is made aware of the need.

The overview screen also shows another patient in bed A 27 of room one of the ward that requires action to be taken by making the bed outline bold. This action may be initiated by the management application 10 in many situations. For example the patient may be waiting for medications or may be having a mild escalation in blood pressure or some other need as determined by the system.

Figure 3:
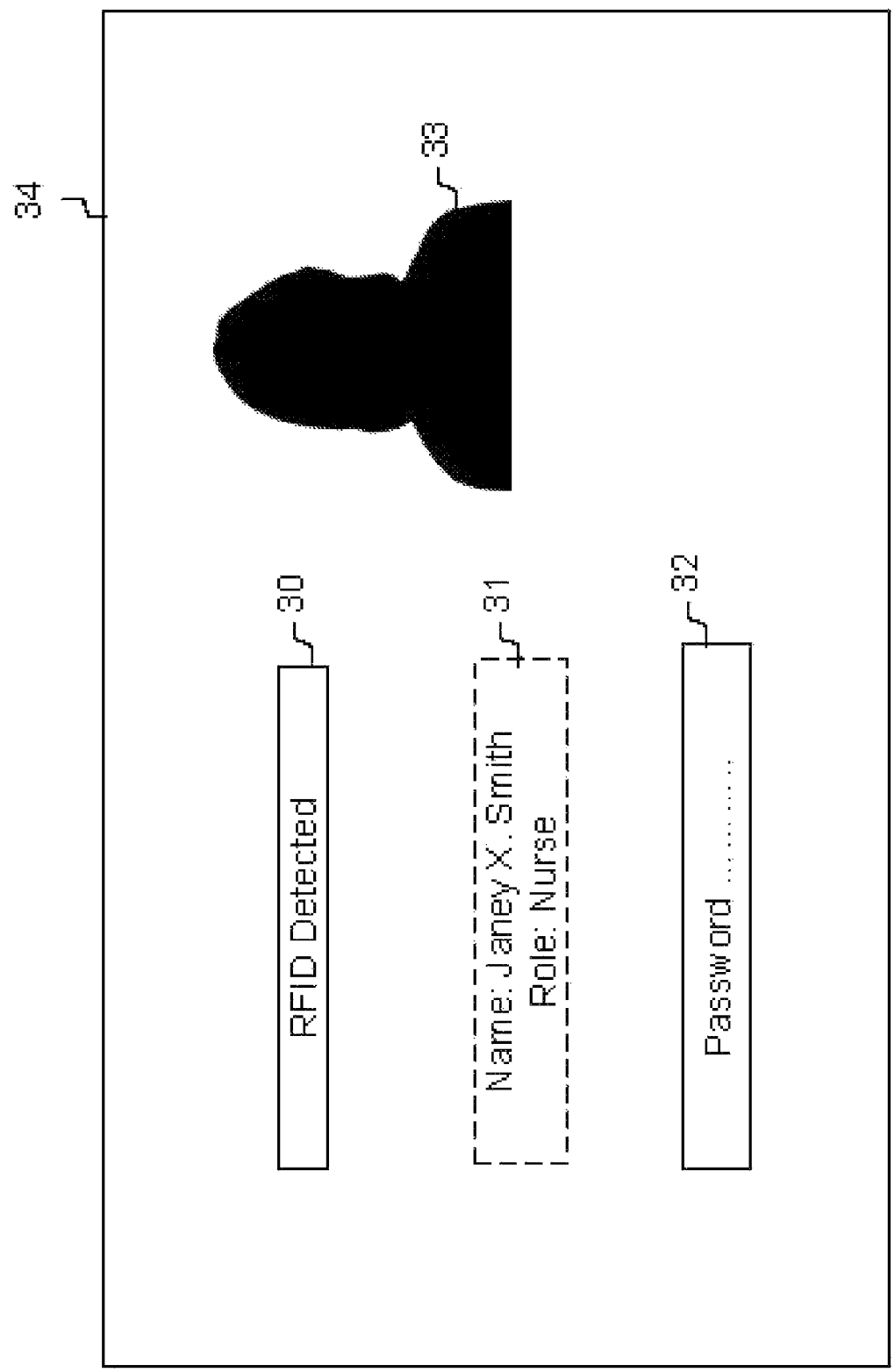
FIG. 3 illustrates an exemplary authentication screen.
Figure 5:
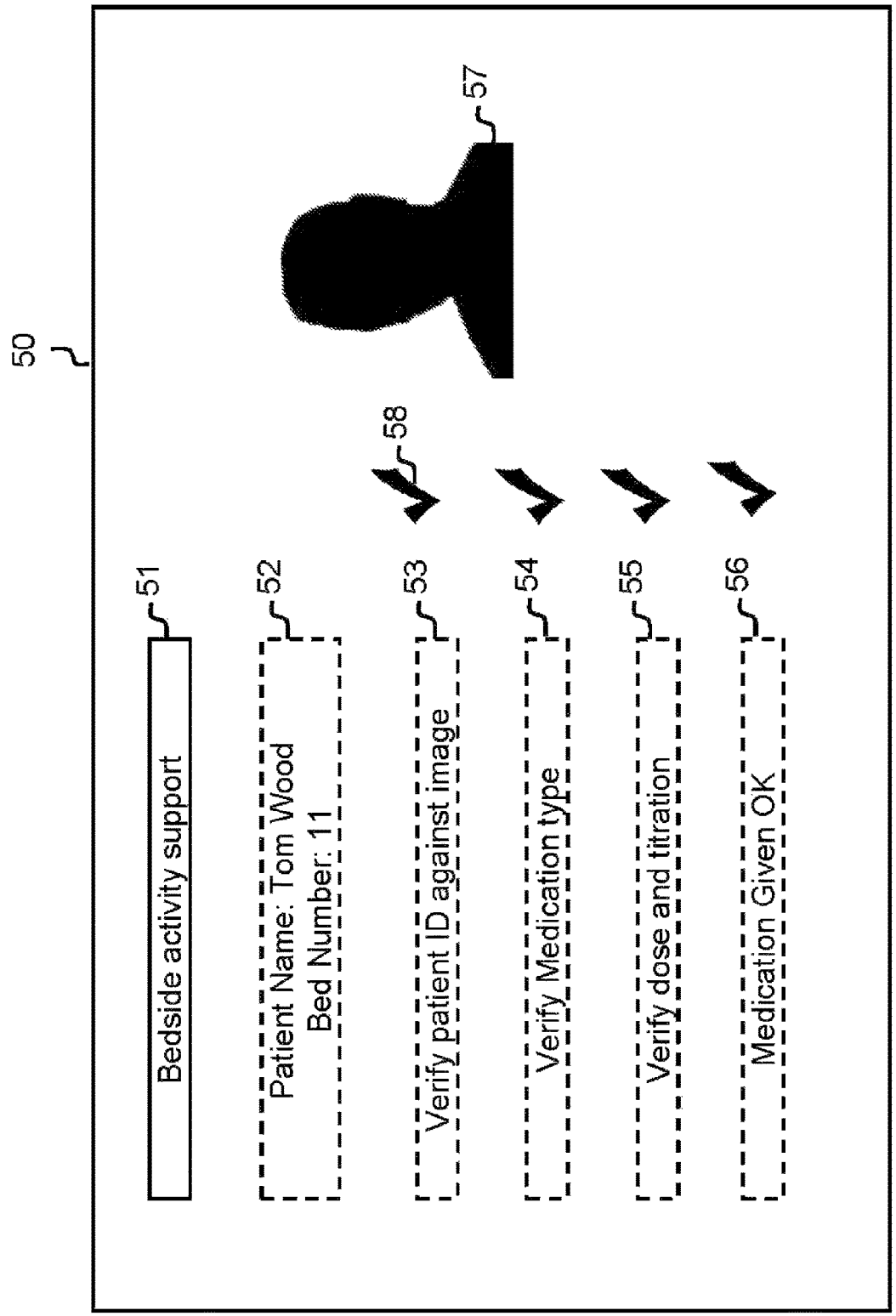
FIG. 5 illustrates an exemplary patient care procedure screen.

FIGS. 3 through 5 represent example screens that are used by the management application 10 to deliver information to the healthcare professionals working on the ward and to obtain feedback and information back from them using touch screen buttons and at times typed or verbally recorded information that is in turn used by the management application 10 to update and re-prioritize the actions and tasks to be done on the patients behalf so that the most effective and efficient care can be taken for each individual patient on a ward within the confines of the resources available on that ward and within the hospital.

Another example of a screen 34 that may be used by the users of the system is described in FIG. 3. This screen 34 may be displayed to nurse as they approach a bed in the ward for the first time in their shift for the day. The RFID tag worn by the nurse is detected 30 by the RFID reader attached to a bedside computer in the ward. The system then asks the nurse to verify their identity by entering their password 32 using a computer keyboard or on screen touch screen keyboard. The nurse verifies their name and role 31 and photograph 33 and then is logged onto the system for the rest of their shift. This process represents one important aspect of the techniques described herein—namely, the process of authenticating the identity of nurses, patients, doctors, specialists and other medical professionals in the hospital.

FIG. 4 describes another screen 40 that is an example of information displayed to a nurse when they approach a patient bed to find out what is the next step or action of care to be done on behalf of the patient. In this example scenario the patients name and bed identity 41 are available for verification. Also the fact that the patient requires medication and that it is available for pickup from the dispensary are noted 41. The system has also determined that there is four minutes left for the medication to be administered within predefined treatment operating procedure guidelines 42 and that a nurse by the name of Janey X. Smith has accepted responsibility for completing this task 43. A further note 44 reminds the nurse to go to the dispensary to pickup the medication is also displayed. The significance of this screen of information delivered by the techniques described herein is that the nurse, doctor or specialist can be provided with contextual support information including procedural advice to help the caregiver effectively help the patient.

FIG. 5 shows an example of a patient care procedure and confirmation screen 50. In this case the screen is called a bedside activity support screen 51. The nurse is then prompted to press a button 53 that confirms that they have verified the patients name 52, photo 57 and bed number 52. When they have clicked this button a check mark is displayed 58 next to the button confirming the action. The nurse is further asked to check the medication type 54, the dose and titration 55 and that the dose has actually been administered to the patient 56. The management application 10 then marks this task as complete and moves the system on to supplying the next service or treatment required by patients on the ward.

Accordingly, the described technique uses inputs from monitors and healthcare professionals to prioritize and actively support the activities involved in the day-to-day care of patients in an institutional healthcare environment. All such activities are supported by rules for the handling of tasks. Roles (such as, for example, nurse, doctor, consultant nurse and patient) set operational limits for each person in the patient care process and presents information supporting the task at hand. In terms of the time and effort required to interact with the system, the majority of activities are designed to require only a single touch on the touch screen, acknowledging the completion of each step in a procedure. The result being an efficient, easy-to operate and effective patient care and management system that automatically generates patient care records/charts. These three capabilities (prioritization, support and recording) are designed to considerably increase the effectiveness and the level of care provided by hospitals and un-encumber healthcare professionals from the time consuming task of keeping and maintaining patient records by using integrated automation wherever possible.

In related aspects, the above-described embodiments refer to inputs from RFID tags, RFID readers and input from bedside touch screen computers. Alternative embodiments may include other devices that may be used to facilitate digital authentication, monitoring and control. In further related aspects, such alternative embodiments may utilize Bar Coding and Bar code reading devices, magnetic stripe technology or bluetooth. None of these technologies offers the suitability to purpose of RFID, as it is suitable for multi-factor authentication as well as proximity detection, is available in a sterilizable form, is long lasting and requires no on-board power to work.

It is noted that the example embodiment described above with reference to FIG. 3, relates to a three-room general patient ward. Alternative embodiments may be applied to any hospital service or even to a whole hospital where every patient and healthcare professional is managed or supported by the system. This system may also be deployed in nursing homes, psychiatric facilities or birthing centers or other facilities where medical care is provided.

In view of exemplary systems shown and described herein, methodologies that may be implemented in accordance with the disclosed subject matter, will be better appreciated with reference to various flow charts. While, for purposes of simplicity of explanation, methodologies are shown and described as a series of acts/blocks, it is to be understood and appreciated that the claimed subject matter is not limited by the number or order of blocks, as some blocks may occur in different orders and/or at substantially the same time with other blocks from what is depicted and described herein. Moreover, not all illustrated blocks may be required to implement methodologies described herein.

Figure 6:
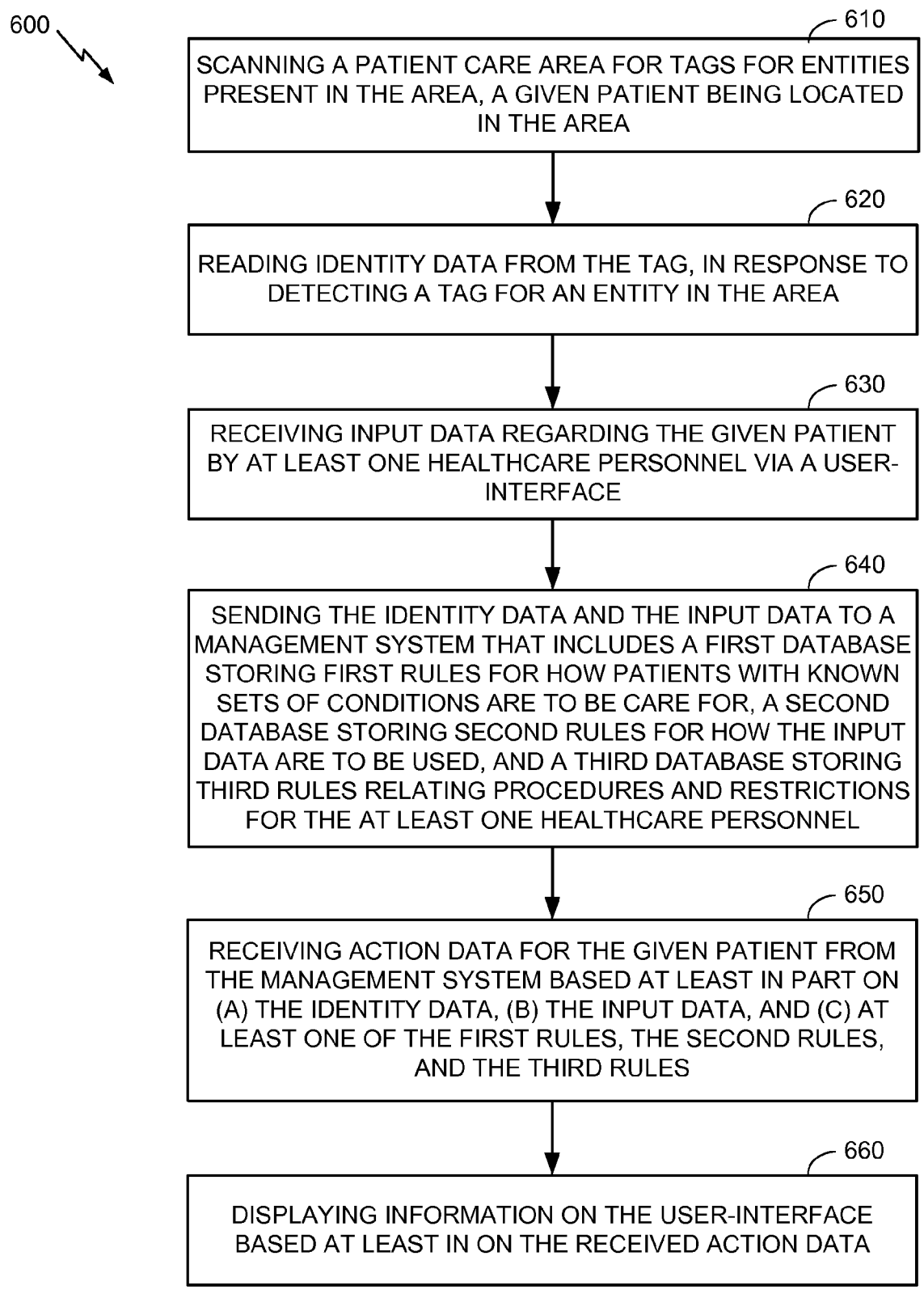
FIG. 6 shows an embodiment of a methodology for healthcare action sequencing by a bedside device.

In accordance with one or more aspects of the subject of this disclosure, there are provided methods for healthcare action sequencing by a bedside device or similar apparatus. With reference to FIG. 6, illustrated is a methodology 600 that may involve, at 610, scanning a patient care area for tags for entities present in the area, a given patient being located in the area. The method 600 may involve, at 620, reading identity data from a tag, in response to detecting the tag for an entity in the area. The method 600 may involve, at 630, receiving input data regarding the given patient by at least one healthcare personnel via a user-interface. The method 600 may involve, at 640, sending the identity data and the input data to a management system that includes a first database storing first rules for how patients with known sets of conditions are to be cared for, a second database storing second rules for how the input data are to be used, and a third database storing third rules relating to procedures and restrictions for the at least one healthcare personnel. The method 600 may involve, at 650, receiving action data for the given patient from the management system based at least in part on (a) the identity data, (b) the input data, and (c) at least one of the first rules, the second rules, and the third rules. The method 600 may involve, at 660, displaying information on the user-interface based at least in on the received action data.

For example, the tag may comprise a radio-frequency identification (RFID) tag, bar-coding, a magnetic stripe, and/or a bluetooth tag. The patient care area may comprise a patient room of a hospital ward. The entity may comprise one of a nurse, a doctor, the given patient, a medication container, and a physical patient file for the given patient.

In related aspects, reading the identity data may involve reading a name, a role, and/or a password for the at least one healthcare personnel from the tag. In further related aspects, the information may include task details for at least one task to be performed by the at least one healthcare personnel. In the alternative, or in addition, the information comprises a patient care procedure and confirmation screen. In yet further related aspects, sending may involve sending the identity data and the input data to the management system via at least one of wireless communication and wired communication. In still further related aspects, the user-interface includes a touch screen interface.

Figure 7:
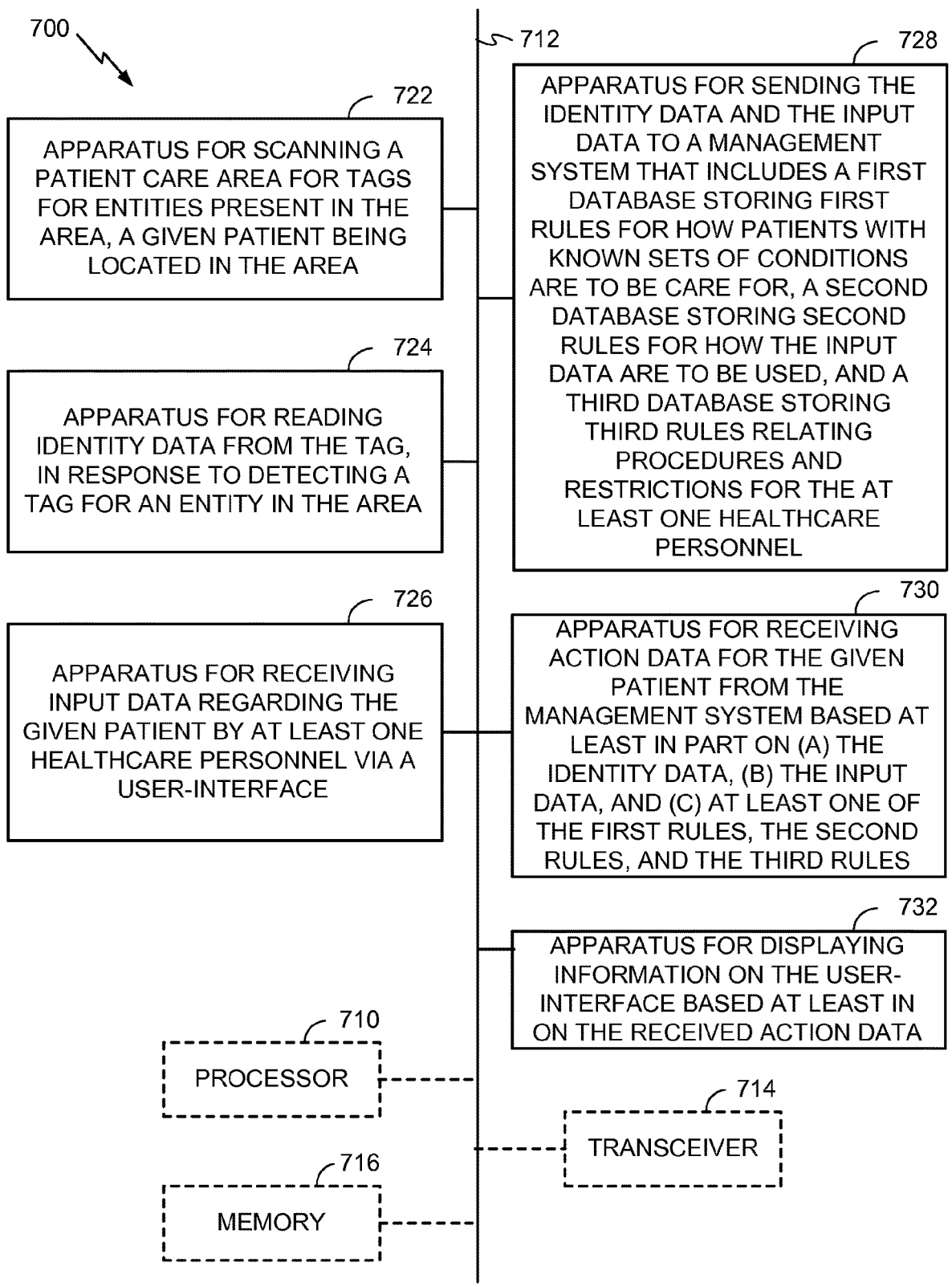
FIG. 7 illustrates an exemplary embodiment of an apparatus for healthcare action sequencing, in accordance with the methodology of FIG. 6.

In accordance with one or more aspects of the embodiments described herein, there are provided devices and apparatuses for healthcare action sequencing, as described above with reference to FIG. 6. With reference to FIG. 7, there is provided an exemplary apparatus 700 that may be configured as a bedside device/computer, or as a processor or similar component for use within the device/computer.

The apparatus 700 may include functional blocks that can represent functions implemented by a processor, software, or combination thereof. As illustrated, in one embodiment, the apparatus 700 may comprise an electrical component or module 722 for scanning a patient care area for tags for entities present in the area, a given patient being located in the area. The apparatus may comprise an electrical component 724 for reading identity data from a tag, in response to detecting the tag for an entity in the area. The apparatus may comprise an electrical component 726 for receiving input data regarding the given patient by at least one healthcare personnel via a user-interface.

The apparatus may comprise an electrical component 728 for sending the identity data and the input data to a management system that includes a first database storing first rules for how patients with known sets of conditions are to be cared for, a second database storing second rules for how the input data are to be used, and a third database storing third rules relating to procedures and restrictions for the at least one healthcare personnel. The apparatus may comprise an electrical component 730 for receiving action data for the given patient from the management system based at least in part on (a) the identity data, (b) the input data, and (c) at least one of the first rules, the second rules, and the third rules. The apparatus may comprise an electrical component 732 for displaying information on the user-interface based at least in on the received action data.

In related aspects, the apparatus 700 may optionally include a processor component 710 having at least one processor, in the case of the apparatus 700 configured as a network entity, rather than as a processor. The processor 710, in such case, may be in operative communication with the components 722-732 via a bus 712 or similar communication coupling. The processor 710 may effect initiation and scheduling of the processes or functions performed by electrical components 722-732.

In further related aspects, the apparatus 700 may include a communication/transceiver component 714. The apparatus 700 may optionally include a component for storing information, such as, for example, a memory device/component 716. The computer readable medium or the memory component 716 may be operatively coupled to the other components of the apparatus 700 via the bus 712 or the like. The memory component 716 may be adapted to store computer readable instructions and data for effecting the processes and behavior of the components 722-732, and subcomponents thereof, or the processor 710, or the methods disclosed herein. The memory component 716 may retain instructions for executing functions associated with the components 722-732. While shown as being external to the memory 716, it is to be understood that the components 722-732 can exist within the memory 716.

Figure 8:
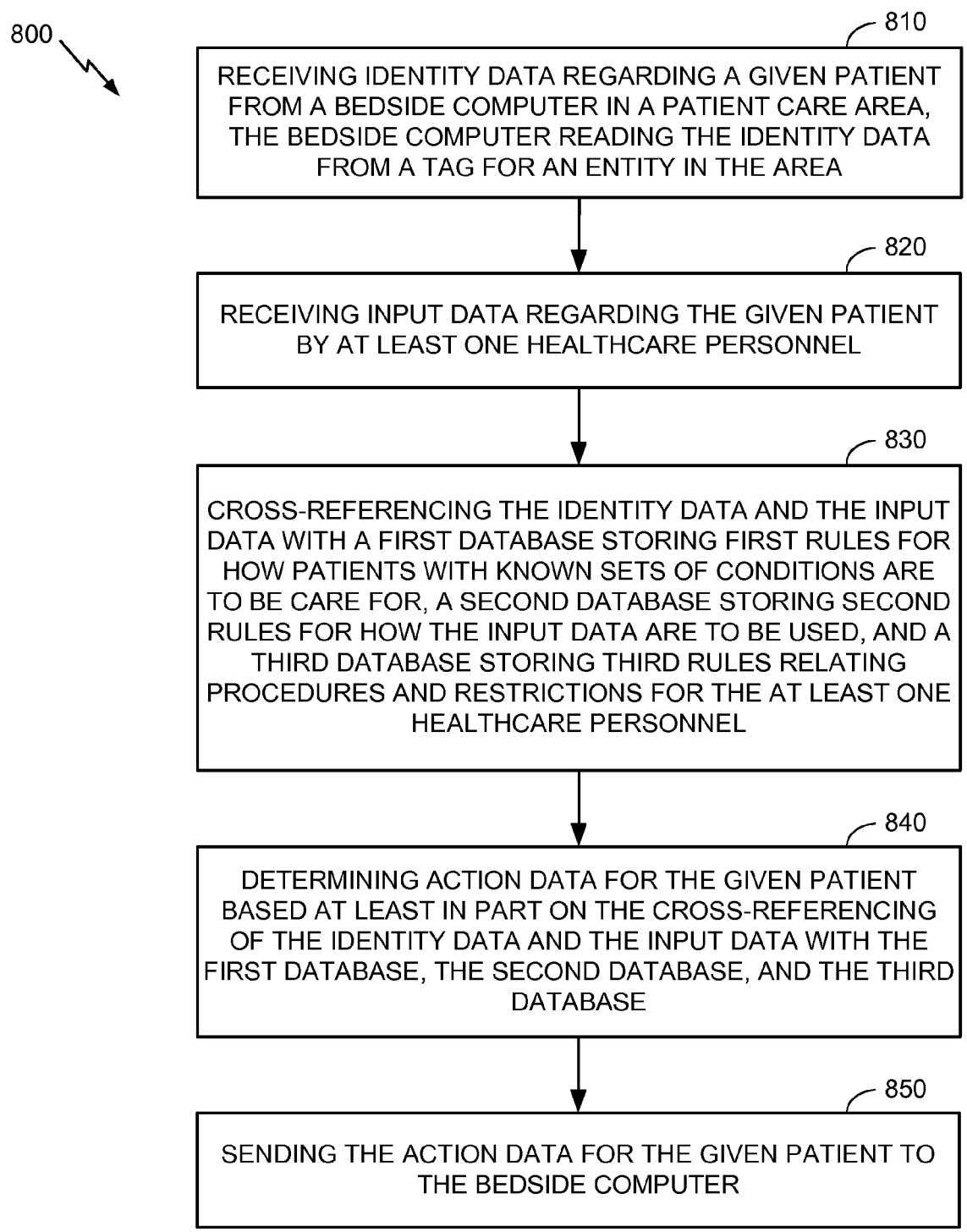
FIG. 8 shows an embodiment of a methodology for healthcare action sequencing by a management system.

In accordance with one or more aspects of the subject of this disclosure, there are provided methods for healthcare action sequencing by a management computer or system. With reference to FIG. 8, illustrated is a methodology 800 that may involve, at 810, receiving identity data regarding a given patient from a bedside computer in a patient care area, the bedside computer reading the identity data from a tag for an entity in the area. The method 800 may involve, at 820, receiving input data regarding the given patient by at least one healthcare personnel. The method 800 may involve, at 830, cross-referencing the identity data and the input data with a first database storing first rules for how patients with known sets of conditions are to be cared for, a second database storing second rules for how the input data are to be used, and a third database storing third rules relating to procedures and restrictions for the at least one healthcare personnel. The method 800 may involve, at 840, determining action data for the given patient based at least in part on the cross-referencing of the identity data and the input data with the first database, the second database, and the third database. The method 800 may involve, at 850, sending the action data for the given patient to the bedside computer.

Figure 9:
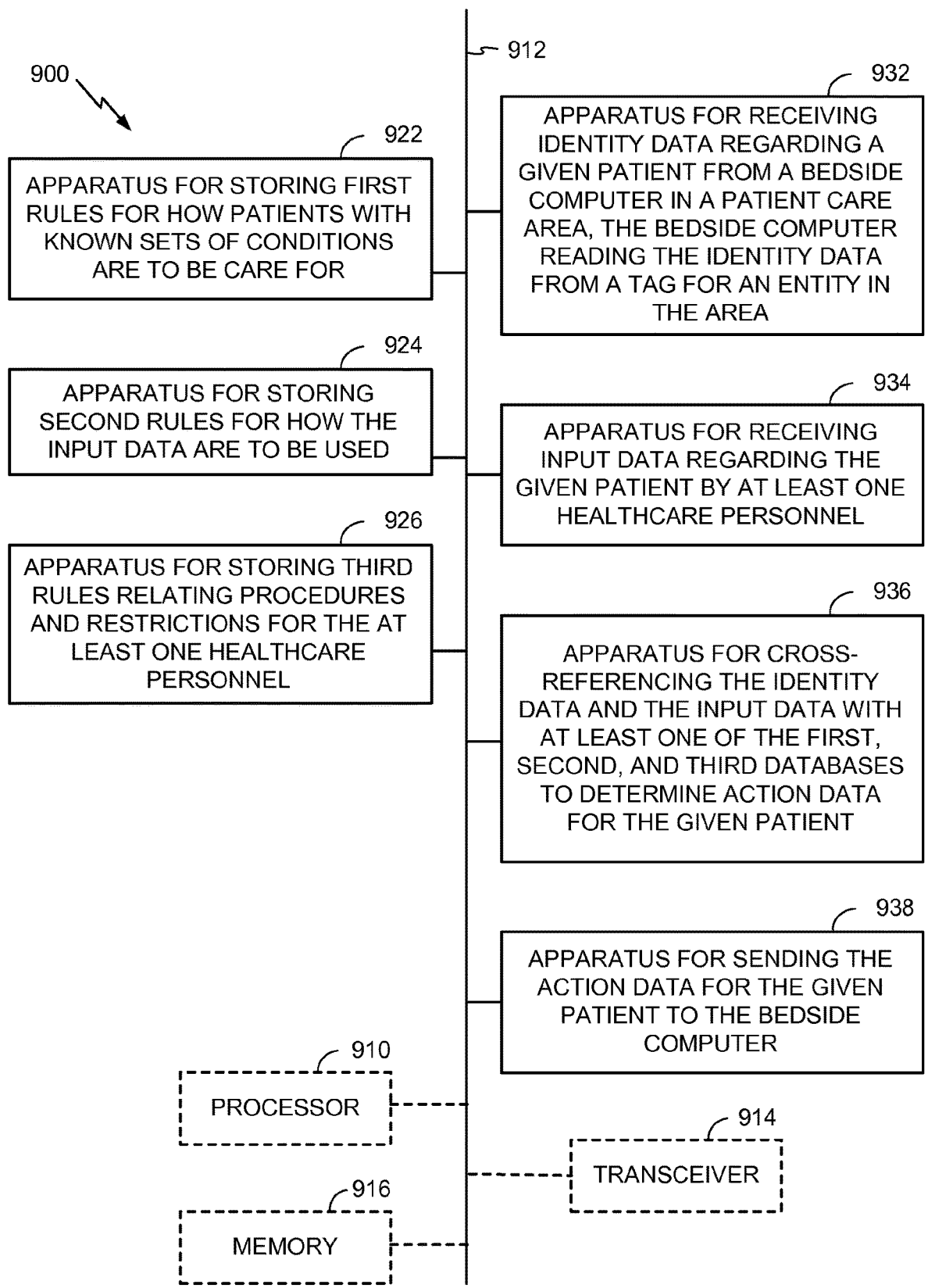
FIG. 9 illustrates an embodiment of an apparatus for healthcare action sequencing, in accordance with the methodology of FIG. 8.

In accordance with one or more aspects of the embodiments described herein; there are provided devices and apparatuses for healthcare action sequencing, as described above with reference to FIG. 8. With reference to FIG. 9, there is provided an exemplary apparatus 900 that may be configured as a management computer/system, or as a processor or similar component for use within the computer/system. The apparatus 900 may include functional blocks that can represent functions implemented by a processor, software, or combination thereof. As illustrated, in one embodiment, the apparatus 900 may comprise an electrical component or module 922 for storing first rules for how patients with known sets of conditions are to be cared for. The apparatus may comprise an electrical component 924 for storing second rules for how the input data are to be used. The apparatus may comprise an electrical component 926 for storing third rules relating to procedures and restrictions for the at least one healthcare personnel.

The apparatus may comprise an electrical component 932 for receiving identity data regarding a given patient from a bedside computer in a patient care area, the bedside computer reading the identity data from a tag for an entity in the area. The apparatus may comprise an electrical component 934 for receiving input data regarding the given patient by at least one healthcare personnel. The apparatus may comprise an electrical component 936 for cross-referencing the identity data and the input data with at least one of the first, second, and third databases to determine action data for the given patient. The apparatus may comprise an electrical component 938 for sending the action data for the given patient to the bedside computer. For the sake of conciseness, the rest of the details regarding apparatus 900 are not further elaborated on; however, it is to be understood that the remaining features and aspects of the apparatus 900 are substantially similar to those described above with respect to apparatus 700 of FIG. 7.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or non-transitory wireless technologies, then the coaxial cable, fiber optic cable, twisted pair, DSL, or the non-transitory wireless technologies are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A method of performing health care actions in respect of multiple patients undergoing health care treatment and located in multiple patient care areas using a management system and a communication device, wherein the communication device comprising a communication device processor and a memory coupled to the communication device processor, the method comprising:

verifying identity of a patient against a list of images grouped in accordance with an area of care and displayed on the communication device, wherein the image, matching the appearance of the patient, is selected preparatory to at least one health care personnel administering at least one health care action to the patient whose image is displayed on the communication device;

receiving, by the communication device, identity data input by the at least one health care personnel regarding verification of patient identity against the image of the patient via a user-interface of the communication device;

receiving, by the communication device, input data input by the at least one health care personnel of the patient via a user-interface of the communication device;

the communication device processor causing the communication device to send the identity data and the input data to the management system, wherein said management system comprises a management application, a management system processor, a first database storing first rules for how patients with known sets of conditions are to be cared for, a second database storing second rules for how the input data are to be used, and a third database storing third rules relating to limitations and operating procedures for the at least one health care personnel;

the management system processor causing the management application to cross-reference the identity data and input data with the first rules, second rules and third rules, update and prioritize actions to be performed in respect of the given patient by the at least one health care personnel, generate an action data for the given patient, wherein said action data is based at least in part on: (a) the identity data, (b) the input data, and (c) at least one of the first rules, the second rules, and the third rules;

sending the action data for the given patient from the management system to the communication device;

receiving, by the communication device, the action data for the given patient from the management system; and the communication device displaying on a user interface information based at least on the received action data wherein said action data requires at least one health care action to be performed by said at least one health care personnel in respect of the given patient being one of the multiple patients located in multiple patient care areas;

wherein said at least one health care action in respect the given patient is performed by said at least one health care personnel; and wherein said at least one health care action is an action of care directly performed on the body of the given patient.

2. The method of claim 1, further comprising:
the communication device processor causing the communication device to display on a user-interface a confirmation screen including information requiring the at least one health care personnel to confirm that said at least one health care action has been performed in respect of the given patient;
receiving, by the communication device via a user-interface, input data by the at least one health care personnel confirming that said at least one health care action has been performed in respect of the given patient; and
the management system processor causing the management system to mark said health care action as complete and/or generate a second action data for the given patient that requires at least one further health care action to be performed by said at least one health care personnel in respect of the given patient.

3. The method of claim 2, wherein a tag is associated with each patient and wherein the tag comprises at least one of a radio-frequency identification (RFID) tag, a bar-coding tag, a magnetic stripe, and a Bluetooth™ tag.

4. The method of claim 3, wherein:
the patient care area comprises a patient room of a hospital ward.

5. The method of claim 3, wherein reading the identity data from the tag by the communication device comprises reading at least one of a name, a role, and a password for the at least one health care personnel from the tag.

6. The method of claim 3, wherein the information comprises task details of the at least one health care action to be performed by the at least one health care personnel in respect of the given patient.

7. The method of claim 3, wherein the information comprises a patient care procedure and confirmation screen.

8. The method of claim 1, further comprising:
the communication device processor causing the communication device to display on a user-interface a confirmation screen including information requiring the at least one health care personnel to confirm that said at least one health care action has been performed on the given patient; and
the management system processor causing the management system to generate an alarm or reminder when
(i) no input data has been received by the communication device computer via a user-interface confirming that said at least one health care action has been performed in respect of the given patient, or
(ii) the at least one health care personnel inputting data into the communication device via a user-interface confirming that said at least one health care action has been performed on the given patient outside health care action guidelines set out in the action data generated by the management application.

9. The method of claim 1, wherein the communication device sending the identity data and the input data to the management system via at least one of wireless communication and wired communication.

10. The method of claim 1, wherein the user-interface comprises a touch screen interface.

11. The method of claim 1, wherein:
the management application sending the action data for the given patient from the management system to the communication device comprises sending the action data via at least one of wireless communication and wired communication; and/or
the communication device receiving the action data for the given patient from the management system comprises receiving the action data via at least one of wireless communication and wired communication.

12. The method of claim 1, wherein the communication device is one of the following devices:
a patient bed side communication device;
a communication device located in a nurse's or doctor's station in a patient care area; or
a communication device located in a dispensary.

13. The method according to claim 1, wherein the third rules stored by the third database relating to limitations and operating procedures for the at least one health care personnel comprise operational limits set based on a role of the at least one health care personnel.

14. The method of claim 1, wherein the at least one health care action comprises administering a medicament to the given patient, and said method comprises the at least one health care personnel administering said medicament directly into the body of said given patient.

15. The method of claim 1, wherein:
the action data requires at least one health care action to be performed by the at least one health care personnel in respect of the given patient without being performed directly onto the body of said given patient; and/or
the step of performing said at least one health care action in respect of the given patient by the at least one health care personnel comprises performing said health care action in relation to said given patient without performing said health care action directly onto the body of said given patient.

16. The method of claim 1, wherein the at least one health care action comprises one or more health care action(s) in relation to the given patient selected from:
(i) administering a medicament to said given patient;
(ii) obtaining, collecting, preparing and/or dispensing a medication to be administered to said given patient;
(iii) verifying a medication required to be administered to the given patient prior to administration of the medication to said given patient;
(iv) verifying and/or recording that a correct medication and/or correct amount or dosage of a medication has been administered to said given patient; and
(v) at least one health care personnel contacting another health care personnel when the health conditions of said given patient change, optionally wherein said at least one health care personnel is a nurse and said another health care personnel is a doctor.

17. A communication device for performing health care actions in respect of multiple patients undergoing health care treatment and located in multiple patient care areas using a management system and said communication device, said communication device comprising:
at least one processor; and
a memory coupled to the at least one processor for storing data;
wherein the at least one processor is configured to:
(i) enable at least one health care personnel to verify patient identity of a patient against an image of the patient displayed on the communication device preparatory to the at least one health care personnel administering at least one health care action to the patient whose image is displayed on the communication device;

(ii) receive by the communication device identity data input by the at least one health care personnel regarding verification of patient identity against the image of the patient via a user-interface of the communication device;

(iii) receive by the communication device input data input by the at least one health care personnel of the patient via a user-interface of the communication device;

(iv) cause the communication device to send the identity data and the input data to a management system, wherein said management system comprises a management application, a management system processor, a first database storing first rules for how patients with known sets of conditions are to be cared for, a second database storing second rules for how the input data are to be used, and a third database storing third rules relating to limitations and operating procedures for the at least one health care personnel, said management system processor is configured to cause the management application to cross-reference the identity data and input data with the first rules, second rules and third rules; update and prioritize actions to be performed in respect of the given patient by the at least one health care personnel; and generate an action data for the given patient, wherein said action data is based at least in part on (a) the identity data, (b) the input data, and (c) at least one of the first rules, the second rules, and the third rules; and send said action data from the management system to the communication device;

(v) receive said action data; and (vi) display information on a user-interface based at least on the received action data, wherein said action data requires at least one health care action to be performed by said at least one health care personnel in respect of the given patient being one of the multiple patients located in multiple patient care areas;

wherein said at least one health care action is an action of care directly performed on the body of the given patient.

18. A management system for performing health care actions in respect of multiple patients undergoing health care treatment and located in multiple patient care areas using a communication device and said management system, said management system comprising:

(a) a first database storing first rules for how patients with known sets of conditions are to be cared for;

(b) a second database storing second rules for how input data regarding a given patient located in a patient care area are to be used;

(c) a third database storing third rules relating to limitations and operating procedures for at least one health care personnel;

(d) a management application;

(e) at least one processor coupled to the first, second, and third databases; and (f) a memory coupled to the at least one processor for storing data;

wherein the at least one processor is configured to:

(i) enable at least one health care personnel to verify patient identity of a patient against an image of the patient displayed on the communication device preparatory to the at least one health care personnel administering at least one health care action to the patient whose image is displayed on the communication device;

(ii) receive by the communication device identity data input by the at least one health care personnel regarding verification of patient identity against the image of the patient via a user-interface of the communication device;

(iii) receive by the communication device input data input by the at least one health care personnel of the patient via a user-interface of the communication device;

(iii) cause the management application to:
cross-reference the received identity data and input data with the first, second, and third databases;
update and prioritize actions to be performed in respect of the given patient by the at least one health care personnel; and
generate an action data for the given patient, wherein said action data is based at least in part on (a) the identity data, (b) the input data, and (c) at least one of the first rules, the second rules, and the third rules;

(iv) send the action data for the given patient from the management system to the communication device for displaying on a user interface information based at least on the action data, wherein the action data requiring at least one health care action to be performed by said at least one health care personnel in respect of the given patient being one of the multiple patients located in multiple patient care areas; and wherein said at least one health care action is an action of care directly performed on the body of the given patient.

19. A non-transitory computer program product for performing health care actions in respect of multiple patients undergoing health care treatment and located in multiple patient care areas using a management system and a communication device comprising a communication device processor and a memory coupled to the communication device processor, said computer program product comprising:

a computer-readable medium comprising code for causing the communication device, with respect to multiple patients located in multiple patient care areas, to (i) enable at least one health care personnel to verify patient identity of a patient against an image of the patient displayed on the communication device preparatory to the at least one health care personnel administering at least one health care action to the patient whose image is displayed on the communication device;

(ii) receive by the communication device identity data input by the at least one health care personnel regarding verification of patient identity against the image of the patient via a user-interface of the communication device;

(iii) receive by the communication device input data input by the at least one health care personnel of the patient via a user-interface of the communication device;

(iv) send the identity data and the input data to a management system, wherein said management system comprises a management application, a management system processor, a first database storing first rules for how patients with known sets of conditions are to be cared for, a second database storing second rules for how the input data are to be used, and a third database storing third rules relating to limitations and operating procedures for the at least one health care personnel, wherein said management system processor is configured to cause the management application to cross-reference the identity data and input data with the first rules, second rules and third rules; update and prioritize actions to be performed in respect of the given patient by the at least one health care personnel; and generate an action data for the given patient, wherein said action data is based at least in part on (a) the identity data, (b) the input data, and (c) at least one of the first rules, the second rules, and the third rules; and send said action data from the management system to the communication device;

(v) receive action data for the given patient from the management system based at least in part on (a) the identity data, (b) the input data, and (c) at least one of the first rules, the second rules, and the third rules; and (vi) display information on the user-interface based at least on the received action data, wherein said action data requires at least one health care action to be performed by said at least one health care personnel in respect of the given patient being one of the multiple patients located in multiple patient care areas; and wherein said at least one health care action is an action of care directly performed on the body of the given patient.

* * * * *